US00PP12688P2

(12) United States Plant Patent
Pouw

(10) Patent No.: US PP12,688 P2
(45) Date of Patent: Jun. 11, 2002

(54) MINIATURE ROSE PLANT NAMED 'RUIPARO'

(75) Inventor: Antonius A. Pouw, De Kwakel (NL)

(73) Assignee: De Ruiter's Nieuwe Rozen B.V., De Kwakel (NL)

( * ) Notice: Subject to any disclaimer, the term of this patent is extended or adjusted under 35 U.S.C. 154(b) by 0 days.

(21) Appl. No.: 09/480,596

(22) Filed: Jan. 10, 2000

(51) Int. Cl.[7] ..... A01H 5/00
(52) U.S. Cl. ..... Plt./122
(58) Field of Search ..... Plt./122

(56) References Cited

U.S. PATENT DOCUMENTS

PP11,099 P * 10/1999 Moore ..... Plt./122

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinctive cultivar of miniature rose plant named 'Ruiparo', characterized by its upright and outwardly spreading growth habit; rapid growth rate; glossy dark green leaves; very freely flowering; large double ruby red-colored flowers; flowers arranged in large sprays; excellent postproduction longevity; and excellent garden performance.

1 Drawing Sheet

BACKGROUND OF THE INVENTION

The present invention relates to a new and distinct cultivar of the miniature rose class, botanically known as *Rosa hybrida*, and hereinafter referred to by the cultivar name Ruiparo.

The new cultivar is a product of a planned breeding program conducted by the Inventor in Hazerswoude, The Netherlands. The objective of the breeding program was to develop compact pot rose varieties with novel and attractive flower colors and excellent postproduction longevity and garden performance.

The new cultivar originated from a cross made by the Inventor of two unnamed proprietary seedlings. The cultivar Ruiparo was discovered and selected by the Inventor as a flowering plant within the progeny of the stated cross in a controlled environment in Hazerswoude, The Netherlands. Plants of the new cultivar differ primarily from plants of the parent seedlings in flower color.

Asexual reproduction of the new cultivar by cuttings taken at Hazerswoude, The Netherlands, has shown that the unique features of this new miniature rose plant are stable and reproduced true to type in successive generations of asexual reproduction.

SUMMARY OF THE INVENTION

The following traits have been repeatedly observed and are determined to be the unique characteristics of 'Ruiparo'. These characteristics in combination distinguish the new miniature rose plant as a new and distinct cultivar:

1. Upright and outwardly spreading growth habit.
2. Rapid growth rate.
3. Glossy dark green leaves.
4. Very freely flowering.
5. Large double ruby red-colored flowers.
6. Flowers arranged in large sprays.
7. Excellent postproduction longevity.
8. Excellent garden performance.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPH

The accompanying colored photograph illustrates typical plants of the new miniature rose plant, showing the colors as true as it is reasonably possible to obtain in colored reproductions of this type. Colors in the photograph may differ slightly from the color values cited in the detailed botanical description which more accurately describe the actual colors of the new miniature rose. The photograph comprises a top perspective view of a large container of multiple plants of the new miniature rose grown in Keller, Tex.

DETAILED BOTANICAL DESCRIPTION

The following observations and measurements describe plants grown in Keller, Tex., in 15-cm containers under outdoor conditions which closely approximate commercial production conditions during the summer and early autumn; plants were about 16 weeks old.

In the following description, color references are made to The Royal Horticultural Society Colour Chart except where general terms of ordinary dictionary significance are used.

Classification:
- *Botanical.*—*Rosa hybrida* cultivar Ruiparo.
- *Commercial.*—Miniature pot rose.

Parentage:
- *Male or pollen parent.*—Unnamed proprietary seedling.
- *Female or seed parent.*—Unnamed proprietary seedling.

Propagation:
- *Type.*—Terminal or stem cuttings.
- *Time to rooting.*—8 to 10 days with soil temperatures of 20° C.

*Rooting habit.*—Propagates easily, roots strong and well-branched.

Plant description:

*Form.*—Upright, outwardly spreading; uniform habit.

*Plant height.*—About 24 cm.

*Plant width.*—About 34 cm.

*Growth habit.*—Vigorous, rapid growth rate. Suitable for 10-cm and larger containers.

*Crop time.*—Time to produce a finished plant in a 10-cm container 20 to 30 cm in height and 15 to 20 cm in width is generally about 10 to 12 weeks depending on average temperature, light level, and cultural practices.

*Stem and lateral branches.*—Branching habit: Freely; branches will potentially form at every node; dense, bushy plants. Diameter of lateral branches, at base: About 3 mm. Internode length: About 1.2 cm. Texture: Smooth, with minute thorns. Color: Darker than 144A. Thorns: Amount: Abundant. Length: About 2 mm, minute. Shape: Roughly deltoid. Color: Brown.

*Foliage description.*—Leaves arranged alternately, compound with typically three to seven leaflets per leaf, generally symmetrical, abundant, and flat to concave in aspect. Stipules at petiole base; stipules about 1 cm in length. Leaflet length: About 2.1 cm. Leaflet width: About 1.5 cm. Shape: Ovate. Apex: Acute to acuminate. Base: Obtuse. Margin: Serrate. Texture, both surfaces: Smooth. Venation pattern: Pinnate. Petiole texture: Smooth, thornless. Petiole length: About 1.7 cm to base of lower leaflet; about 3.8 cm to base of terminal leaflet. Petiole diameter: About 1 mm. Color: Young foliage, upper surface: 147A. Young foliage, lower surface: 147B. Mature foliage, upper surface: 147A. Mature foliage, lower surface: 147B. Venation, both surfaces: Similar to ground color. Petiole: Close to 147A to 147B.

Flower description:

*Flower type and habit.*—Large double ruby red flowers. Consistently symmetrical rosette flowers that are hemispherical in shape. Very freely and continuously flowering. The flowers are borne singly on peduncles and arranged in large sprays with about three flowers per spray. Flowers persistent.

*Flowering season.*—Year-round under greenhouse conditions, optimal flowering from spring through autumn under garden conditions.

*Flower diameter.*—About 4.3 cm.

*Flower depth (height).*—About 2 cm.

*Flower longevity on plant.*—About 12 to 14 days.

*Fragrance.*—Faint, typical of Rosa.

*Flower buds (stage of showing color).*—Shape: Ovoid. Length: About 1.5 cm. Diameter: About 1 cm. Color: 57A to 57B.

*Petals.*—Quantity: About 30 per flower; typically about six rows. Length, outer petals: About 2.4 cm. Width, outer petals: About 2.5 cm. Shape: Roughly cordate. Apex: Accuminate. Base: Obtuse. Margin: Entire. Texture: Smooth, velvety. Color: When opening, upper surface: Richer and deeper red, but close to 53B. When opening, lower surface: Richer and deeper red, but close to 53B to 53C. Fully opened, upper surface: Richer and deeper red, but close to 53A; becoming darker, richer and deeper than 61A with subsequent development. At very base of petals, white, closest to 155D. Fully opened, lower surface: 53C to close to 59B.

*Sepals.*—Quantity: Typically five per flower. Length: About 2.3 cm. Diameter: About 5 mm. Shape: Narrowly ovate. Apex: Sharply pointed. Base: Truncate. Texture: Pubescent, fine white hairs on upper surface; prickles on lower surface. Color: Upper surface; 144A; covered with fine white hairs. Lower surface: 144A.

*Peduncles.*—Strength: Good yet flexible. Aspect: Erect. Length: About 3.1 cm. Color: 144A with faint reddish, close to 59A, overtones.

*Reproductive organs.*—Stamens: Quantity: About 25 per flower. Anther size: About 2.5 by 1.5 mm. Anther shape: Bilobate. Anther color: 13A. Pistils: Quantity: About 25 per flower. Style length: About 4 mm. Style color: 4D with red, 59A, overtones towards apex.

*Seed.*—Seed production has not been observed.

Disease resistance: Plants of the new miniature rose have been shown to be resistant to Powdery Mildew.

Weather tolerance: Plants of the new miniature rose have been observed to tolerate temperatures from −5 to 43° C.

It is claimed:

1. A new and distinct miniature rose plant named 'Ruiparo', as illustrated and described.

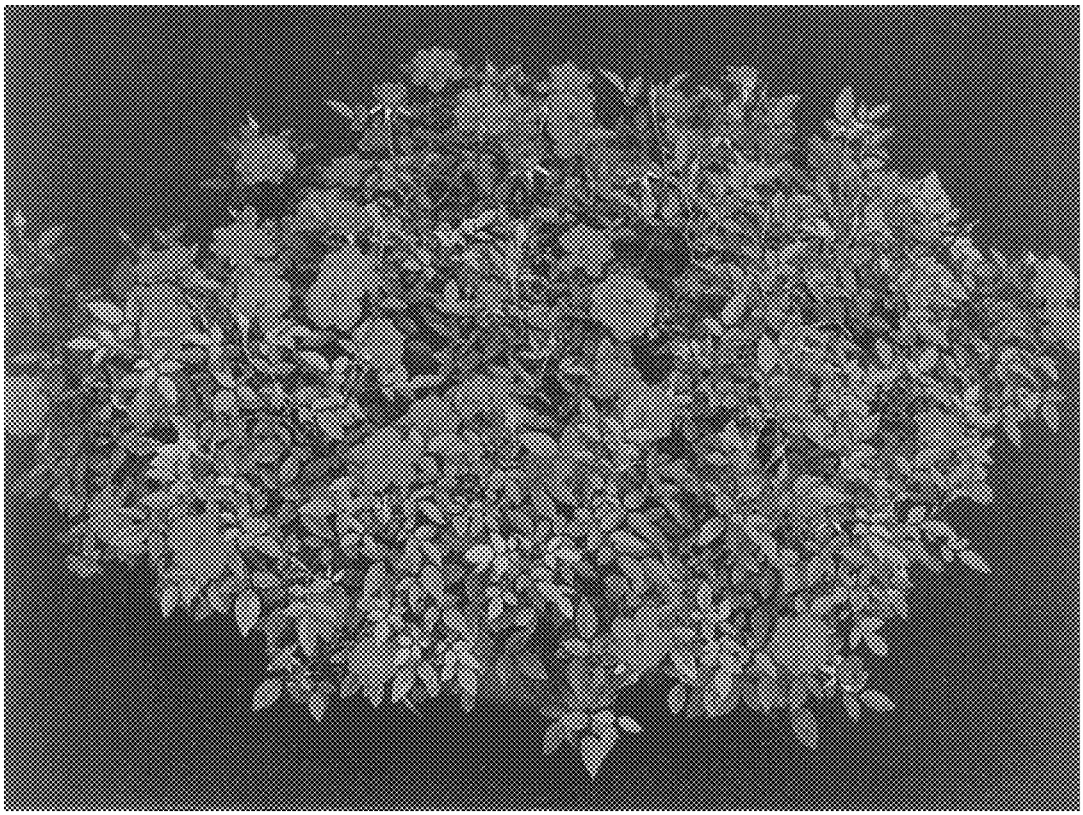

* * * * *